United States Patent [19]

Reichert et al.

[11] Patent Number: 5,358,707
[45] Date of Patent: Oct. 25, 1994

[54] OXIDIZED VARIANTS OF GM-CSF

[75] Inventors: Paul Reichert, Montville; Gail F. Seelig, Watchung; Paul P. Trotta, Secaucus, all of N.J.

[73] Assignee: Schering Corporation, Kenilworth, N.J.

[21] Appl. No.: 867,186

[22] PCT Filed: Jan. 4, 1991

[86] PCT No.: PCT/US91/00007
§ 371 Date: Jun. 25, 1992
§ 102(e) Date: Jun. 25, 1992

[87] PCT Pub. No.: WO91/10684
PCT Pub. Date: Jul. 25, 1991

Related U.S. Application Data

[63] Continuation-in-part of Ser. No. 462,180, Jan. 8, 1990, abandoned.

[51] Int. Cl.$^5$ .............................................. A61K 45/05
[52] U.S. Cl. ......................................... 424/85.1; 530/351
[58] Field of Search ..................... 530/351, 402, 410; 424/85.1

[56] References Cited

U.S. PATENT DOCUMENTS 5,116,943 5/1992 Koths et al. ..................... 530/351
5,200,327 4/1993 Garvin et al. .................... 435/69.5

FOREIGN PATENT DOCUMENTS 2002389 1/1990 Japan.

OTHER PUBLICATIONS

Fukita, et al., Chem. Abstracts 113:35453d (1990).
Gough, et al., Nature 309:763 (1984).
Greenberg, et al., Current Microbiol. 17:321 (1988).
Ohgami, et al., J. Biotechnol. 12:219 (1989).

*Primary Examiner*—Michael G. Wityshyn
*Assistant Examiner*—C. Sayala
*Attorney, Agent, or Firm*—Paul G. Lunn; Norman C. Dulak; Steinar V. Kanstad

[57] ABSTRACT

Biologically active oxidized variants of granulocyte-macrophage colony stimulating factor (GM-CSF) are provided in which one or more methionine residues are oxidized. Methods are also provided for making and characterizing such variants.

14 Claims, 1 Drawing Sheet

Fig. 1

```
Ala - Pro - Ala - Arg - Ser - Pro - Ser - Pro -
         10
Ser - Thr - Gln - Pro - Trp - Glu - His - Val -
                   20
Asn - Ala - Ile - Gln - Glu - Ala - Arg - Arg -
                              30
Leu - Leu - Asn - Leu - Ser - Arg - Asp - Thr -
                                          40
Ala - Ala - Glu - Met - Asn - Glu - Thr - Val -
Glu - Val - Ile - Ser - Glu - Met - Phe - Asp -
         50
Leu - Gln - Glu - Pro - Thr - Cys - Leu - Gln -
                   60
Thr - Arg - Leu - Glu - Leu - Tyr - Lys - Gln -
                              70
Gly - Leu - Arg - Gly - Ser - Leu - Thr - Lys -
                                          80
Leu - Lys - Gly - Pro - Leu - Thr - Met - Met -
Ala - Ser - His - Tyr - Lys - Gln - His - Cys -
         90
Pro - Pro - Thr - Pro - Glu - Thr - Ser - Cys -
                   100
Ala - Thr - Gln - Ile - Ile - Thr - Phe - Glu -
                              110
Ser - Phe - Lys - Glu - Asn - Leu - Lys - Asp -
                                          120
Phe - Leu - Leu - Val - Ile - Pro - Phe - Asp -
Cys - Trp - Glu - Pro - Val - Gln - Glu
```

OXIDIZED VARIANTS OF GM-CSF

The present application is the United States national application corresponding to International Application No. PCT/US 91/00007, filed Jan. 4, 1991, and designating the United States, which PCT application is in turn a continuation-in-part of U.S. application Ser. No. 07/462,180, filed Jan. 8, 1990, now abandoned the benefit of which applications is claimed pursuant to the provisions of 35 U.S.C. §§120, 363 and 365(C).

BACKGROUND OF THE INVENTION

The control of blood cell formation is mediated by a group of glycoproteins called colony stimulating factors. One such protein is granulocyte-macrophage colony stimulating factor (GM-CSF), which stimulates progenitor cells to form granulocyte, macrophage and eosinophil colonies on semisolid medium [Lopez et al., J. Clin. Invest. 78: 1220 (1986); Metcalf, Blood 67: 257 (1986)]. GM-CSF can stimulate the initial cell divisions of erythroid progenitor cells without altering their ultimate ability to form mature red cells [Sieff et al., Science, 230: 1171 (1985)]. It also can stimulate colon), formation in the HL60 and KG-1 human myeloid leukemic cell lines [Tomonaga et al., Blood 67: 31 (1986)]and has a direct effect on neutrophil function [Lopez et al., J. Clin. Invest. 78: 1220 (1986)].

The cloning and sequencing of complementary DNAs encoding human [Lee et al., Proc. Natl. Acad. Sci. USA 82: 4360 (1985); Wong et al., Science 228: 810 (1985); Cantrell et al., Proc. Natl. Acad. Sci. USA 82: 6250 (1985)], gibbon [Wong et al., supra and murine [Gough et al., Nature 309: 763 (1984)]GM-CSF have been reported. Greenberg et al. [Current Microbiol. 17: 321 (1988)]have described the expression of biologically active, mature human GM-CSF in an E. Coli secretory expression system. The isolation of natural GM-CSF from cultured human [U.S. Pat. No. 4,438,032; Gasson et al., Science 230: 1171 (1985); Burgess et al., Blood 69: 43 (1987)], mouse [Burgess et al., Exp. Hematol. 9: 893 (1981); Sparrow et al., Proc. Natl. Acad. Sci. USA 82: 292 (1985)] and rat [Wu et al., Exp. Hematol. 12: 267 (1984)] cells has also been reported.

Mature human GM-CSF consists of about 127 amine acid residues, four of which are methionine residues. The mature forms of mouse and gibbon GM-CSF appear to contain only three methionine residues. GM-CSF from various species is also known to contain a number of cysteine residues, and the human protein contains four.

Methionine and cysteine are often important to the overall conformation and biological activity of a protein. The side chains of methionine residues are hydrophobic and tend to associate with other hydrophobic residues in the stable conformation of a protein. The sulfhydryl groups of cysteines are often joined in disulfide linkages (as cystine), which also serve to maintain conformation.

Under oxidizing conditions, the character of methionine and cysteine residues changes markedly. The sulfur in methionine is converted from a thio ether to a highly polar sulfoxide or sulfone. If a given methionine was associated with other hydrophobic residues, there is a likelihood that the hydrophilic oxidized form will no longer do so. Oxidation of cysteine residues can give rise to unnatural intra- and inter-chain disulfide bridges. The possible overall effect of the oxidation of a protein can thus be a dramatic change in conformation (3-dimensional shape) which can result in a strong reduction or complete loss of biological activity. Whether a given protein will be thus altered by oxidation cannot presently be predicted with any reasonable degree of certainty.

SUMMARY OF THE INVENTION

It has surprisingly been found that the methionine residues of GM-CSF can be oxidized to a high degree while retaining a significant amount of biological activity, as determined in an in vitro bioassay. This invention provides such oxidized variants of GM-CSF.

More particularly, this invention provides biologically active oxidized variants of GM-CSF having at least one oxidized methionine residue, which variants are essentially free of unoxidized GM-CSF and other oxidized variants. Variants are provided in which one, two, three or four oxygen atoms are introduced into the methionine residues of GM-CSF. At least about 30% of the biological activity of the unoxidized protein is retained in these variants. Some of the variants are essentially as active as unoxidized GM-CSF.

This invention further provides methods for making and characterizing the oxidized GM-CSF variants.

The oxidized GM-CSF variants of this invention can be used in any indication for which unoxidized GM-CSF itself can be used, such as for acquired immunodeficiency syndrome (AIDS) [Groopman et al., N. Engl. J. Meal. 317: 593 (1987); Baldwin et al., Proc. Natl. Acad. Sci. USA 85: 2763 (1988)], myelodysplastic syndrome [Vadan-Raj et al., N. Engl. J. Med. 317: 1545 (1987)]and bone marrow transplantation [Monroy et al., Blood 70: 1096 (1987)].

Although the variants possess a significant amount of the biological activity of unoxidized GM-CSF, some of them have different receptor binding characteristics. As a consequence, they may have different pharmacokinetic properties in vivo which may be beneficial from a therapeutic perspective. Moreover, because the methionine residues of the protein have been altered by oxidation, the GM-CSF variants of the invention may also have greater stability and resistance to proteolytic degradation and clearance in vivo. Because the biological activity of the most highly oxidized variant of the invention is substantially lower than that of the other variants or of unoxidized GM-CSF, it could be useful as an antagonist.

BRIEF DESCRIPTION OF THE FIGURE

This invention can be more readily understood by reference to accompanying FIG. 1, which shows the amino acid sequence of mature, human GM-CSF.

DESCRIPTION OF THE INVENTION

All references cited herein are hereby incorporated in their entirety by reference.

As used herein, "GM-CSF" means a protein which (a) has an amino acid sequence that is substantially identical to the sequence of mature (i.e., lacking a signal peptide) human GM-CSF shown in FIG. 1 and (b) has biological activity that is common to native GM-CSF.

Substantial identity of amino acid sequences means that the sequences are identical or differ by one or more amino acid alterations (deletions, additions, substitutions) that do not substantially impair biological activity. For example, Schrimsher et al. [Biochem. J 247: 195

(1987)]have disclosed a human GM-CSF variant in which the methionine residue at position 80 has been replaced by an isoleucine residue. GM-CSF of other species such as-mice and gibbons (which contain only 3 methionines) and rats are also contemplated by this invention. Recombinant GM-CSFs produced in prokaryotic expression systems may also contain an additional N-terminal methionine residue, as is well known in the art. Any GM-CSF meeting the substantial identity requirement is included, whether glycosylated (i.e., from natural sources or from a eukaryotic expression system) or unglycosylated (i.e., from a prokaryotic expression system or chemical synthesis).

GM-CSF for use in this invention can be obtained from natural sources (U.S. Pat. No. 4,438,032; Gasson et al., supra; Burgess et al., supra; Sparrow et al., supra; Wu et al., supra), by the use of recombinant DNA methodology (Wong et al., supra, Lee et al., supra; Cantrell et al., supra; Gough et al., supra; Greenberg et al., supra; and International Patent Application Publication Nos. WO 86/00639, WO 86/03225, WO 87/02060 and WO 89/00582) or by chemical synthesis based upon the published GM-CSF amino acid sequences.

Recombinant and natural human and murine GM-CSFs are also articles of commerce, available for purchase, e.g., from Genzyme Corporation, Boston, Mass.

In the chemical synthetic approach, GM-CSF is synthesized by a suitable method such as by exclusive solid phase synthesis, partial solid phase methods, fragment condensation or classical solution synthesis. The protein is preferably prepared by solid phase peptide synthesis as described by Merrifield, J. Am. Chem. Soc. 85: 2149 (1963). The synthesis is carried out with amino acids that are protected at the alpha-amino terminus. Trifunctional amino acids with labile side-chains are also protected with suitable groups to prevent undesired chemical reactions from occurring during the assembly of the GM-CSF. The alpha-amino protecting group is selectively removed to allow subsequent reaction to take place at the amino-terminus. The conditions for the removal of the alpha-amino protecting group do not remove the side-chain protecting groups.

The alpha-amino protecting groups are those known to useful in the art of stepwise polypeptide synthesis. Included are acyl type protecting groups (e.g., formyl, trifluoroacetyl, acetyl), aromatic urethane type protecting groups [e.g., benzyloxycarbonyl (Cbz), substituted benzyloxycarbonyl and 9-fluorenylmethyloxycarbonyl (Fmoc)], aliphatic urethane protecting groups (.e.,g. t-butyloxycarbonyl (Boc), isopropyloxycarbonyl, cyclohexyloxycarbonyl) and alkyl type protecting groups (e.g., benzyl, triphenylmethyl). The preferred protecting group is Boc. The side-chain protecting groups for Tyr include tetrahydropyranyl, tert.-butyl, trityl, benzyl, Cbz, 4-Br-Cbz and 2,6-dichlorobenzyl. The preferred side-chain protecting group for Tyr is 2,6-dichlorobenzyl. The side-chain protecting groups for Asp include benzyl, 2,6-dichlorobenzyl, methyl, ethyl and cyclohexyl. The preferred side-chain protecting group for Asp is cyclohexyl. The side-chain protecting groups for Thr and Ser include acetyl, benzoyl, trityl, tetrahydropyranyl, benzyl, 2,6-dichlorobenzyl and Cbz. The preferred protecting group for Thr and Ser is benzyl. The side-chain protecting groups for Arg include nitro, Tos, Cbz, adamantyloxycarbonyl and Boc. The preferred protecting group for Arg is Tos. The side-chain amino group of Lys may be protected with Cbz, 2-Cl-Cbz, Tos or Boc. The 2-Cl-Cbz group is the preferred protecting group for Lys.

The side-chain protecting groups selected must remain intact during coupling and not be removed during the deprotection of the amino-terminus protecting group or during coupling conditions. The side-chain protecting groups must also be removable upon the completion of synthesis, using reaction conditions that will not alter the finished protein.

Solid phase synthesis is usually carried out from the carboxyl-terminus by coupling the alpha-amino protected (side-chain protected) amino acid to a suitable solid support. An ester linkage is formed when the attachment is made to a chloromethyl or hydroxymethyl resin, and the resulting protein will have a free carboxyl group at the C-terminus. Alternatively, when a benzhydrylamine or p-methylbenzhydrylamine resin is used, an amide bond is formed and the resulting protein will have a carboxamide group at the C-Terminus. These resins are commercially available, and their preparation has described by Stewart et al., "Solid Phase Peptide Synthesis" (2d Edition), Pierce Chemical Go., Rockford, Ill., 1984.

The C-terminal amino acid, protected at the side-chain if necessary and at the alpha-amino group, is coupled to the benzhydrylamine resin using various activating agents including dicyclohexylcarbodiimide (DCC), N,N'-diisopropylcarbodiimide and carbonyldiimidazole. Following the attachment to the resin support, the alpha-amino protecting group is removed using trifluoroacetic acid (TFA) or HCl in dioxane at a temperature between 0° and 25° C. Dimethylsulfide is added to the TFA after the introduction of methionine (Met) to suppress possible S-alkylation. After removal of the alpha-amino protecting group, the remaining protected amino acids are coupled stepwise in the required order to obtain the desired sequence.

Various activating agents can be used for the coupling reactions including DCC, N,N'-diisopropylcarbodiimide, benzotriazol-1-yl-oxy-tris-(dimethylamino)-phosphonium hexafluorophosphate (BOP) and DCC-hydroxybenzotriazole (HOBt). Each protected amino acid is used in excess (>2.0 equivalents), and the couplings are usually carried out in N-methylpyrrolidone (NMP) or in DMF, $CH_2Cl_2$ or mixtures thereof. The extent of completion of the coupling reaction is monitored at each stage, e.g., by the ninhydrin reaction as described by Kaiser et al., Anal. Biochem. 34: 595 (1970). In cases where incomplete coupling is found, the coupling reaction is repeated. The coupling reactions can be performed automatically with commercially available instruments.

After the entire assembly of the GM-CSF, the protein is cleaved with a reagent such as liquid HF for 1-2 hours at 0° C., which cleaves the protein from the resin and removes all side-chain protecting groups. A scavenger such as anisole is usually used with the liquid HF to prevent cations formed during the cleavage from alkylating the amino acid residues present in the protein. The protein-resin may be deprotected with TFA/dithioethane prior to cleavage if desired.

Side-chain to side-chain cyclization on the solid support requires the use of an orthogonal protection scheme with enables selective cleavage of the side-chain functions of acidic amino acids (e.g., Asp) and the basic amino acids (e.g., Lys). The 9-fluoroenylmethyl (Fm) protecting group for the side-chain of Asp and the 9-fluorenylmethyloxycarbonyl (Fmoc) protecting group for the side-chain of Lys can be used for this purpose. In these cases, the side-chain protecting groups of the Boc-protected protein-resin are selectively removed with piperidine in DMF. Cyclization is achieved on the solid support using various activating agents including DCC, DCC/HOBt or BOP. The HF reaction is carried out on the cyclized protein-resin as described above.

GM-CSF from whatever source can be purified using standard methods including but not limited to acid or salt precipitation, ion-exchange chromatography, metal chelate chromatography, gel filtration, fast protein liquid chromatography (FPLC), high performance liquid chromatography (HPLC), preparative disc gel or curtain electrophoresis, isoelectric focusing, low temperature organic solvent fractionation, countercurrent distribution and immunoaffinity chromatography.

The oxidized GM-CSF variants of the invention can be isolated from natural sources or from recombinant DNA expression systems, or they can be prepared by chemical oxidation of unoxidized GM-CSF, recombinant or otherwise.

It has been found, for example, that GM-CSF prepared in an *E. coli* secretory expression system as described by Greenberg et al., supra, contains GM-CSF variants having one or two oxidized methionine residues. These variants can be isolated using standard methods or as detailed below. Most of the material produced in such systems, however, is unoxidized GM-CSF.

Greater quantities of oxidized variants can be produced by recombinant means, e.g., by growing *E. coli* auxotrophs in medium containing oxidized methionine (i.e., methionine sulfoxide or methionine sulfone). Replacement methionine with a methionine analog has been described by Cowie et al., [Biochem. Biophys. Acta 26: 252 (1957)].

Chemical oxidation of unoxidized GM-CSF can be carried out, e.g., using $H_2O_2$, BNPS-Skatole (2-(2-nitrophenylsulfenyl)-3-methyl-3-bromoindolenine), performic acid, sodium periodate or chloramine T. The use of $H_2O_2$ is preferred.

Recombinant, mature human GM-CSF produced in *E. coli* contains four methionine residues at positions 36, 46, 79 and 80 (counting from the amino-terminus; see FIG. 1). It has been found that with $H_2O_2$ as the oxidizing agent at a neutral pH, three oxygen atoms can readily be added to the protein. Methionine 79 or 80 is oxidized most readily, followed in succession by methionines 46 and 36. Addition of a fourth oxygen atom at methionine 79 or 80 is preferably carried out at a low pH.

The oxidized variants of mature human GM-CSF having one, two, three and four oxygen atoms are designated MET-$O^1$, MET-$O^2$, MET-$O^3$ and MET-$O^4$, respectively, although of course variants produced from substantially identical GM-CSFs (as defined above) may have more or fewer total oxygen atoms, depending upon their methionine content and degree of oxidation. Some recombinant GM-CSFs produced in prokaryotic expression systems may also contain an additional amino-terminal methionine residue which can be oxidized.

Oxidation using $H_2O_2$ is carried out at a concentration of from about 0.02 to about 2% (vol/vol), preferably about 0.2%, $H_2O_2$ and from about 0.25 to about 10 mg/ml GM-CSF. When recombinant mature human GM-CSF is used, the oxidation reaction is allowed to proceed for about 1 to about 60 minutes at a pH of about 6 to about 8 and a temperature of about 4 to about 37° C., to make MET-$O^1$ and MET-$O^2$. Reaction at room temperature for about 5 minutes at pH 7 is preferred. MET-$O^3$ is made by carrying out the reaction at the same temperature and pH but for a period from about 2 to about 20 hours. This reaction is conveniently allowed to proceed overnight. Preparation of MET-$O^4$ from recombinant human GM-CSF is preferably carried out at the same $H_2O_2$ concentration and temperature but for a period of from about 2 to about 20 hours at a pH of from about 0.5 to about 5. Overnight reaction at a pH of about 3 is preferred. The oxidation reactions can be terminated, e.g., by the addition of sufficient catalase to decompose the $H_2O_2$.

The oxidized variants can be separated from each other and from unoxidized GM-CSF using the above-mentioned protein purification methods, although reversed-phase FPLC/HPLC is preferred, using a support such as a C-4, C-8 or C-18 support with about a 300 angstrom (300 A) pore size and a gradient of an organic solvent such as acetonitrile or propanol.

Characterization of the purified, oxidized GM-CSF variants can readily be achieved by analyzing for added oxygen content. This can be done by a two-step process comprising (a) digesting a variant with a proteolytic enzyme to produce a peptide digest and (b) subjecting the peptide digest to fast-atom bombardment mass spectrometry (FAB/MS) as described by Biemann [Int. J. Mass Spectrom. Ion Phys. 45: 183 (1982)].

Digestion can be carried out using a proteolytic enzyme or chemical cleavage method having a defined specificity. For example, trypsin specifically cleaves proteins at the carboxyl side of lysine and arginine residues. Chymotrypsin is specific for cleavage at tyrosine, phenylalanine and tryptophan residues. *Staphylococcus aureus* strain $V_8$ protease is specific for the carboxyl side of glutamic acid residues.

Selection of a protease(s) for the digestion of a given oxidized variant should preferably be made so that each of the peptides formed contains as few methionine residues as possible. In some cases, the use of two or more proteases may be required to characterize a variant as fully as possible. For example, MET-$O^2$ was analyzed by subjecting a sample of this variant to digestion with trypsin followed by FAB/MS, and then subjecting a second sample to V8 protease digestion followed by FAB/MS.

This dual enzyme digestion was required because trypsin digestion produced a mixture of peptides in which residues 36 and 46 were both present in one peptide and residues 79 and 80 were together in another. V8 protease digestion, in contrast, produced a mixture of peptides in which residues 36 and 46 were in separate peptides. By combining the data obtained from the two digests, it was possible to determine more accurately where the two oxygen atoms had been added in MET-$O^2$.

Those of skill in the art, knowing the amino acid sequence of a GM-CSF upon which a variant is based and knowing the specificities of the available proteases, can readily determine which enzymes(s) to use to maximally characterize the variant.

Which methionine residue(s) in a given variant has received one or more oxygen atoms can be determined by carrying out a parallel digestion(s) on the unoxidized GM-CSF used to make the variant and subjecting the digest(s) to FAB/MS. All of the peptides from the unoxidized protein will produce peaks in FAB/MS which correspond to the expected masses of the peptides. These masses can be easily calculated knowing the specificity of the enzyme(s) used and the formula weights of the amino acid residues in the peptides. In contrast, expected masses of one or more peptides containing a methionine residue(s) from an oxidized variant will not be present in FAB/MS where a methionine residue(s) has been oxidized. Instead, FAB/MS will reveal one or more new peaks which are some multiple of 16 (mass of an oxygen atom) greater in mass then expected for the unmodified peptides, depending upon how many oxygen atoms have been added.

Oxidized methionine residues containing one extra atom of oxygen are methionine sulfoxides (—SO—); those with two are methionine sulfones (=$SO_2$).

Characterization of glycosylated oxidized variants of GM-CSF from natural sources or from eukaryotic expression systems can be carried out in similar fashion, except that the carbohydrate is preferably removed first. Carbohydrates can be removed enzymatically from such variants using known methods.

Pharmaceutical compositions can be prepared which contain effective amounts of one or more of the oxidized GM-CSF variants of the invention and a physiologically acceptable carrier. Such carriers are well known to those skilled in the art. The variants can be administered directly or in the form of a composition to a human patient for the treatment of acquired immunodeficiency syndrome or myelodysplastic syndrome, or for bone marrow transplantation or other indications in which unoxidized GM-CSF can be used. The pharmaceutical compositions are made by admixing a physiologically acceptable carrier with an effective amount of one or more of the variants.

Determination of the proper dosage of an oxidized GM-CSF variant for a particular situation is within the skill of the art. Generally, treatment is initiated with smaller dosages that are less than optimum. Thereafter, the dosage is increased by small increments until the optimum effect under the circumstances is reached. For convenience, the total daily dosage may be divided and administered in portions during the day if desired.

The amount and frequency of administration of the oxidized GM-CSF variants of the invention will be regulated according to the judgment of the attending clinician, taking into account such factors as age, condition and size of the patient and severity of the symptom(s) being treated.

EXAMPLES

Unless otherwise specified, percentages given below for solids in solid mixtures, liquids in liquids, and solids in liquids are on a wt/wt, vol/vol and wt/vol basis, respectively. Protein analyses were carried out using a Bradford dye binding assay (Bio-Rad Labs, Richmond. Calif.) using bovine serum albumin as a standard.

Preparation of Chemically Oxidized GM-CSF Variants

Recombinant mature human GM-CSF was produced in *E. coli* essentially as described by Greenberg et al. [Current Microbiol. 17: 321 (1988)] and purified as described by Trotta et al. in International Patent Application Publication No. WO 89/00579.

A solution containing 2.5 mg/ml GM-CSF in 20 mM sodium phosphate buffer, pH 7.0, was oxidized by making the solution 200 mM in hydrogen peroxide (0.2%). Reaction was allowed to proceed at 25° C. for 5 minutes for MET-$O^1$ and MET-$O^2$, and overnight for MET-$O^3$. The reactions were quenched by the addition of 0.025% (wt/wt) catalase.

MET-$O^4$ was prepared as described above, except that the pH of the solution was adjusted to 3.0 with $H_3PO_4$ and the reaction was carried out overnight.

The quenched reaction mixtures were purified in a 20 ml bed volume $C_2/C_8$, 300A pore size column (Pharmacia, Piscataway, N.J.) equilibrated with 0.1% trifluoroacetic acid (TFA) in 35% acetonitrile. The column was developed at a flow rate of 2.5 ml/minute with a linear gradient of 35 to 45% acetonitrile over a one-hour period. The eluant was monitored at 280 nm with a Pharmacia UV-1 fixed wavelength detector, and 0.5 ml fractions were collected. MET-$O^1$, MET-$O^2$, MET-$O^3$ and MET-$O^4$ eluted at acetonitrile concentrations of 42, 44, 41 and 40%, respectively. Peak fractions were pooled and concentrated by lyophilization for further analysis. Integration of peaks obtained from analytical HPLC using the same system showed that the isolated variants were all greater than 90% pure.

Analysis for Oxygen Content

Samples of unoxidized GM-CSF and the purified oxidized variants were desalted by reversed phase HPLC chromatography in a 1×10 mm Aquapore RP 300 column. The column had been equilibrated with solution A [0.1% aqueous trifluoroacetic acid (TFA)] and was developed by a gradient comprising 5 minutes of solution A containing 45% solution B (0.1% TFA, 90% acetonitrile) followed by 25 minutes of solution A containing 65% solution B. The flow rate was 0.05 ml/minute, and the eluant was monitored spectrophotometrically at 215 nm. The organic solvent was removed from pooled fractions by lyophilization.

Samples of the desalted variants and unoxidized GM-CSF containing 10 mg/ml protein were subjected to digestion by either TPCK-treated trypsin (Sigma Chemical Co., St. Louis, Mo.) or *S. aureus* strain V8 protease (Boehringer Mannheim) for 18 hours at 37° C. in 0.1M $NH_4HCO_3$, about pH 8.1 (degassed). The substrate to enzyme ratio in both cases was 25.

The digests were degassed in vacuo and dithiothreitol was added to 10 mM. The samples were flushed with nitrogen gas for 5 minutes, sealed and incubated for 60 minutes at 40° C. and then for 5 minutes at 100° C. The samples were concentrated to 15 μl with nitrogen gas. FAB/MS was then performed on the samples, essentially as described by Biemann, supra.

Briefly, FAB/MS was carried out on a Model ZAB-SE (VG Instrument Analytical, Ltd., Manchester, England) high mass ultra-high resolution instrument. The samples were applied to the probe tip, covered by a thin layer of glycerol/thioglycerol and then mixed thoroughly with a Pasteur pipette prior to insertion into the source. The samples were ionized by bombardment with Xenon atoms produced by a saddle-field ion source operating with a tube current of 1 mA at an energy of 6–8 Kev. The mass spectrometer was operated at an accelerating potential of 8 Kev, and the calibration of the instrument was carried out with a cesium chloride standard.

Results of the proteolytic digestions—FAB/MS analyses are shown in Tables 1 and 2, where the peptides produced are shown in sequence, from the amino termini of the intact proteins. The amino acid sequences of the peptides are shown in the standard single-letter abbreviated form (Lehninger, Principles of Biochemistry, 1982, Worth Publishers Inc., New York, p. 96).

Expected peptide masses are shown by a +; values higher than expected due to oxygen addition are indicated numerically. All of the expected masses were observed for the peptides from the digestion of unoxidized GM-CSF.

were analyzed and compared using the Prosec computer program from AVIV Associates. Far UV analysis was carried out at a scanning range of 260–185 nm with a cell path of 0.2 mm and a sample concentration of 0.2 mg/ml in 20 mM sodium phosphate buffer, pH 7.2. Near

TABLE 1
Tryptic Peptide Analysis

| Peptide No. | Sequence | Calculated Mass | Observed Masses for MET- | | | |
|---|---|---|---|---|---|---|
| | | | $O^1$ | $O^2$ | $O^3$ | $O^4$ |
| 1 | A—P—A—R | 413 | + | + | + | + |
| 2 | S—P—S—P—S—T—Q—P—W—E—H—V—N—A—I—Q—E—A—R | 2134 | + | + | + | + |
| 3 | A—L—L—N—L—S—R | 714 | + | + | + | + |
| 4 | D—T—A—A—E—M—N—E—T—V—E—V—I—S—E—M—F—D—L—Q—E—P—T—C—L—Q—T—R | 3201 | + | 3218 | 3233 | 3233 |
| 5 | L—E—L—Y—K | 664 | + | + | + | + |
| 6 | Q—G—L—R | 472 | + | + | + | + |
| 7 | G—S—L—T—K | 504 | + | + | + | + |
| 8 | L—K | 259 | + | + | + | + |
| 9 | G—P—L—T—M—M—A—S—H—Y—K | 1235 | 1251 | 1251 | 1251 | 1267 |
| 10 | Q—H—C—P—P—T—P—E—T—S—C—A—T—Q—I—I—T—F—E—S—F—K | 2465 | + | + | + | + |
| 11 | E—N—L—K | 502 | + | + | + | + |
| 12 | D—F—L—L—V—I—P—F—D—C—W—E—P—V—Q—E | 1950 | + | + | + | + |

TABLE 2
V8 Peptide Analysis

| Peptide No. | Sequence | Calculated Mass | Observed Masses for MET- | | | |
|---|---|---|---|---|---|---|
| | | | $O^1$ | $O^2$ | $O^3$ | $O^4$ |
| 1 | A—P—A—R—S—P—S—P—S—T—Q—P—W—E | 1151 | + | + | + | + |
| 2 | H—V—N—A—I—Q—E | 810 | + | + | + | + |
| 3 | A—R—R—L—L—N—L—S—R—D—T—A—A—E | 1586 | + | + | + | + |
| 4 | M—N—E | 392 | + | + | 408 | 408 |
| 5 | T—V—E— | 347 | + | + | + | + |
| 6 | V—I—S—E | 446 | + | + | + | + |
| 7 | M—F—D—L—Q—E | 782 | + | 798 | 798 | 798 |
| 8 | P—T—C—L—Q—T—R—L—E | 1060 | + | + | + | + |
| 9 | L—Y—K—Q—G—L—R—G—S—L—T—K—L—K—G—P—L—T—M—M—A—S—H—Y—K—Q—H—C—P—P—T—P—E | 3712 | 3728 | 3728 | 3728 | 3744 |
| 10 | T—S—C—A—T—Q—I—I—T—F—E | 1213 | + | + | + | + |
| 11 | S—F—K—E | 510 | + | + | + | + |
| 12 | N—L—K—D—F—L—L—V—I—P—F—D—C—W—E | 2306 | + | + | + | + |
| 13 | P—V—Q—E | 472 | + | + | + | + |
| 14 | M—F—D—L—Q—E—P—T—C—L—Q—T—R—L—E* | 1824 | + | 1840 | 1840 | 1840 |

*Peptide No. 14 was formed due to incomplete digestion and corresponds to peptides 7 and 8.

Taken together, the data of Tables 1 and 2 show that MET-$O^1$ contains 1 oxygen atom at methionine 79 or 80; MET-$O^2$ contains 1 oxygen atom at methionine 79 or 80 and one at methionine 46; MET-$O^3$ contains one oxygen atom at methionine 79 or 80 and one each at methionines 36 and 46; and MET-$O^4$ contains two oxygen atoms at methionine 79 and/or 80 and one each at methionines 36 and 46. The oxidized methionines in MET-$O^1$, MET-$O^2$ and MET-$O^3$ must be methionine sulfoxides. Methionines 36 and 46 in MET-$O^4$ must also be methionine sulfoxides, but it is unclear whether the other two oxygens in this variant are in the form of methionine sulfoxides at positions 79 and 80 or in the form of a methionine sulfone at one of these positions.

Further Physical Characterization of MET-$O^3$ and MET-$O^4$

To further characterize MET-$O^3$ and MET-$O^4$ and to compare them with unoxidized GM-CSF, both variants and the unoxidized protein (all at least 90% pure) were subjected to circular dichroism (CD), nuclear magnetic resonance (NMR) and sodium dodecylsulfate polyacrylamide gel electrophoresis (SDS PAGE).

CD spectra were obtained in the near and far ultraviolet regions using a Jasco J-500A spectropolarimeter interfaced through an IF-500 to an IBM PC. The data UV analysis was performed at a scanning range of 400–250 nm with a 1 cm cell path and a sample concentration of 0.2 mg/ml in 20 mM sodium phosphate buffer, pH 7.0 (MET-$O^3$) or 7.28 (MET-$O^4$).

In the far UV region, the spectrum of MET-$O^3$ was similar to that of the unoxidized GM-CSF. MET-$O^4$, however, showed a shift in the negative region from 207 to 205 nm, an indication of a more random structure. In the near UV region, the spectra of MET-$O^3$ and unoxidized GM-CSF were similar except that the spectrum of the variant showed an increased intensity in the 261 to 268 nm negative region, and the cutoff region for the variant from positive to negative ellipticity was shifted to a higher wavelength, The near UV spectrum for MET-$O^4$ was markedly different from that of the unoxidized protein. An intense band at 289 nm was diminished, there was slight broadening in the 350–300 mn region, and changes were observed in the phenylalanine transitions at 261 to 268 nm and in the tyrosine transition at 275 nm.

Proton NMR was recorded at 400 MHz on a Varian XL-400 at 25° C. Samples for NMR were deuterated by lyophilizing from excess $D_{2O}$, first 98.8% and then 99.96% $D_{2O}$. The pDs of the solutions were adjusted to 7.28 with deuterated sodium hydroxide and deuterium chloride. Typically, 500–1,000 free induction decays were added with a 5,000 Hz spectral width and 10,000 data points. Line broadening of 0.5 HZ was routinely done prior to Fourier transformation. Samples were run in 5 mm NMR tubes, and an external standard of deuterated TSP (sodium 3-Trimethylsilylpropionate-2,2,3,3-$d_4$) was used.

Comparing MET-$O^3$ and MET-$O^4$ to unoxidized GM-CSF, significant changes were observed in the methionine to methionine sulfoxide shift from 2.0 to 2.8 ppm. Marked changes were also observed in the aromatic region (7.0–7.7 ppm) and in the region near 6 ppm, suggesting effects on tyrosine or tryptophan residues.

Sodium dodecylsulfate polyacrylamide gel electrophoresis (SDS PAGE) was carried out essentially as described by Laemmli [Nature 227: 680 (1970)], using 15% polyacrylamide gels. Samples of all four of the purified variants and unoxidized GM-CSF containing about 5 to 15 μg of protein were treated with 0.01% 2-mercaptoethanol in a boiling water bath for 2 minutes, after which they were applied to a 15 cm slab gel and run for 5 hours at 15 mA. Phosphorylase B (92,500 daltons), bovine serum albumin (67,000 daltons), ovalbumin (45,000 daltons), carbonic anhydrase (31,000 daltons), soybean trypsin inhibitor (21,500 daltons) and β-lactalbumin (14,400 daltons) were run as molecular weight marker proteins (mixture from Pharmacia, Piscataway, N.J.).

MET-$O^1$, MET-$O^2$, MET-$O^3$ and MET-$O^4$ migrated with apparent molecular weights of 16,200, 16,700, 18,200 and 18,200 daltons, respectively, in the SDS PAGE. Unoxidized GM-CSF migrates with an apparent molecular weight of 14,800 daltons in the same system.

To demonstrate the reversibility of the oxidation reaction, a 75 μg sample of MET-$O^4$ was diluted in 30 ml of 5% aqueous acetic acid, and 7.5 μl of 20% N-methyl mercaptoacetamide were added. The mixture was heated at 40° C. under a nitrogen atmosphere for 24 hours, after which the solution was evaporated to dryness and the sample was subjected to SDS PAGE as described above. The migration of the MET-$O^4$ thus treated was coincident with the migration of unoxidized GM-CSF.

Isolation and Characterization of Oxidized Variants of GM-CSF from a Microbial Expression System Recombinant, mature human GM-CSF was produced in an *E. coli* secretory expression system essentially as described by Greenberg et al., supra. Following fermentation, the cells were disrupted and a soluble extract was prepared as described by Trotta et al., supra. This extract was then purified by HPLC.

A sample of the extract containing about 200 mg of protein in 50 ml of 20 mM sodium phosphate buffer, pH 7.0, was loaded onto a 4.1×250 cm bed Rainin Dynamax C4 (300 A) column which had been equilibrated with 27% aqueous acetonitrile, 0.1% TFA. The column was run at 22° C. at a flow rate of 30 ml/minute and developed with a linear gradient 27 to 72% acetonitrile in 0.1% TFA over a 30 minute period. The effluent was monitored spectrophotometrically at 280 nm using a Knauer variable wave length detector, and fractions were collected manually based upon the UV absorption profile.

Fractions containing GM-CSF and oxidized variants designated $V_1$ and $V_2$ were pooled, diluted 3-fold with 27% aqueous acetonitrile, 0.1% TFA and rechromatographed separately in a 2.1×250 cm bed Rainin Dynamax C4 (300 A) column as above at a flow rate of 10 ml/min. The column was developed using a linear gradient of 27 to 72% acetonitrile in 0.1% trifluoroacetic acid over a 30 minute period, and 0.5 ml fractions were collected. The fractions were monitored by SDS PAGE as described above and by analytical HPLC (using the same resin and solvent system). Fractions containing oxidized variants $V_1$ and $V_2$ were pooled to yield 1.3 mg of $V_1$ and 1.7 mg of $V_2$.

Using the above procedures, unoxidized recombinant GM-CSF (designated $V_0$) and oxidized variants $V_1$ and $V_2$ were all obtained in greater than 90% purity. Samples of $V_0$, $V_1$ and $V_2$ were subjected to SDS PAGE, where it was found that the apparent molecular weights of $V_0$, $V_1$ and $V_2$ were 14,750, 16,250 and 16,700 daltons, respectively. Mass spectral analysis of tryptic and V8 proteolytic digests prepared as described above showed that $V_2$ contained one additional oxygen atom at position 79 or 80 and another at position 46. On this basis, $V_2$ was similar to MET-$O^2$.

Gas-phase amino-terminal amino acid sequencing carried out essentially as described by Hewick et al. [J. Biol. Chem. 256: 7990 (1981)] revealed that both proteins had the Ala-Pro-Ala-Arg-Ser-Pro-Ser-Pro-Ser-Thr-Gln- amino terminus characteristic of mature human GM-CSF. Amino acid composition analysis carried out as described by Blankenship et al., [Anal. Biochem. 178: 227 (1989)] showed that the composition of $V_2$ was indistinguishable from that of $V_0$. Analytical isoelectric focusing performed essentially as described by O'Farrel [J. Biol. Chem. 250: 4007 (1975)] revealed no significant differences between $V_0$, $V_1$ and $V_2$; all had a pI of about 5.3.

Biological and Receptor Binding Activity

Bioassay of unoxidized mature human GM-CSF and the oxidized MET-$O^3$, MET-$O^4$, $V_1$ and $V_2$ variants was carried out essentially as described by Mossmann [J. Immunol. Methods 65: 55 (1983)], using KG-1 cells (ATCC CCL 246). Briefly, cultures of about $1 \times 10^4$ cells were incubated with dilutions of the various proteins in Iscove's modified Dulbecco's medium at 37° C. for 6 days. The tetrazolium salt MTT (3-[4,5-Dimethylthiazol-2-yl]-2,5-diphenyltetrazolium bromide; Thiazolyl blue) was then added at a final concentration of 0.5 mg/ml, and incubation was continued for another 4 hours. MTT is cleaved by mitochondrial dehydrogenase enzymes to produce a colored reaction product, formazan, the quantity of which is directly related to $LOG_2$ cell concentration. The amount of formazan in the culture media was measured spectrophotometrically at 570 nm, and the titer of the various oxidized and unoxidized GM-CSF samples was determined by comparing the dilutions producing 50% maximal cell growth stimulation to an amount of a standard GM-CSF solution which produced a similar stimulation. The results are shown in Table 3.

TABLE 3

| Protein | KG-1 Cell Bioassay Biological Activity | |
|---|---|---|
| | (Units/mg × $10^{-9}$) | (% GM-CSF Activity) |
| GM-CSF | $2.9^a$ | 100 |
| MET-$O^3$ | $2.8^a$ | 97 |
| MET-$O^4$ | $0.9^a$ | 31 |
| GM-CSF | $5.3^a$ | 100 |
| $V_1$ | $2.6^b$ | 49 |

TABLE 3-continued

| | KG-1 Cell Bioassay Biological Activity | |
|---|---|---|
| Protein | (Units/mg × 10⁻⁹) | (% GM-CSF Activity) |
| V₂ | 3.1[b] | 58 |

[a]Data shown are the mean of 5 determinations.
[b]Data shown are the mean of 12 determinations.

Analysis of the MET-O³ and MET-O⁴ variants was carried out at a different time than the analysis of the $V_1$ and $V_2$ variants. Therefore, in Table 3, data obtained for the variants are also expressed as a percentage of the unoxidized GM-CSF specific bioactivity to facilitate comparison. As shown in Table 3, all of the oxidized variants possessed significant biological activity.

Mature, human ¹²⁵I-GM-CSF was prepared for use in a receptor binding assay essentially as described by Bolton et al. [Biochem. J. 133: 529 (1973)], using ¹²⁵I-Bolton-Hunter reagent from New England Nuclear. Briefly, 2 mCi (2,000 Ci/mmole) of ¹²⁵I-Bolton-Hunter reagent in a 200 μl volume; was dried by a gentle stream of nitrogen. Fifteen micrograms of purified GM-CSF dissolved in 100 μl of 0.1M sodium borate, pH 8.5, were added to the reaction vessel. The reaction was allowed to proceed for 1 hour at 22° C., after which unreacted Bolton-Hunter reagent was quenched with 200 μl of 1M glycine.

The radioiodinated protein was separated from unreacted labeling reagent by gel filtration in a PD 10 column (Pharmacia, Piscataway, N.J.) equilibrated with the sodium borate buffer containing 0.1% gelatin. The labeled GM-CSF had a specific radioactivity of about $3 \times 10^6$ μCi/μmole, as determined by the self displacement method of Cairo et al. [Biochem. J. 212: 259 (1983)].

To carry out receptor binding analysis on MET-O³ and MET-O⁴, samples of both variants and unoxidized GM-CSF were prepared in binding buffer (0.1M sodium borate buffer, pH 8.5, containing 0.25% gelatin). The receptor assay employed a standard mixture of $5 \times 10^8$ KG-1 cells in 0.26 ml of Iscove's modified Dulbecco's medium (GIBCO) containing 10% fetal calf serum (GIBCO). Assays were carried out by adding aliquots of binding medium with or without varying amounts of unoxidized GM-CSF, MET-O³ or MET-O⁴ to the cells; adding binding buffer to a final volume of 0.4 ml for each sample, and incubating the samples for 10 minutes at 22° C. Following this incubation, 250 μl aliquots of binding buffer containing $2.14 \times 10^{-14}$ moles (about 27,000 cpm) of ¹²⁵I-GM-CSF were added to each mixture and incubation was continued for an additional 2 hours at 22° C.

The mixtures were then centrifuged at 600×g for 2.5 minutes to sediment the cells. The supernatant fluids were discarded and the pellets were resuspended in Iscove's modified Dulbecco's medium and centrifuged twice as described above. The cell pellets were then counted in a gamma counter, with the results shown in Table 4.

TABLE 4

| Competitive Displacement of ¹²⁵I-GM-CSF from KG-1 Cells by Oxidized and Unoxidized GM-CSF | |
|---|---|
| Protein | Kd (× 10¹²)[a] |
| GM-CSF | 11.2 ± 3.4 |
| MET-O³ | 19.8 ± 3.2 |
| MET-O⁴ | 40.5 ± 5.0[b] |

[a]The data were analyzed using the ligand program of Munson et al. [Anal. Biochem. 197:220, (1980)].
[b]The value shown is the average of two determinations.

The data of Table 4 show that the Kds of MET-O³ and MET-O⁴ were about twice and four times that of unoxidized GM-CSF, respectively.

Many modifications and variations of this invention may be made without departing from its spirit and scope, as will become apparent to those skilled in the art. The specific embodiments described herein are offered by way of example only, and the invention is to be limited only by the terms of the appended claims.

What is claimed is:

1. A biologically active oxidized GM-CSF variant having at least one oxidized methionine residue, which variant is essentially free of unoxidized GM-CSF.

2. The oxidized GM-CSF variant of claim 1 which is a human GM-CSF variant.

3. The oxidized GM-CSF variant of claim 1 which is produced by chemical oxidation of an unoxidized GM-CSF.

4. The oxidized GM-CSF variant of claim 1 which is produced by purification of an extract from a microbial expression system expressing a gene encoding GM-CSF.

5. The oxidized GM-CSF variant of claim 4 which is produced by a wild-type *E. coli* bacterium incorporating methionine into proteins.

6. The oxidized GM-CSF variant of claim 4 which is produced by an *E. coli* methionine auxotroph incorporating oxidized methionine into proteins.

7. The oxidized GM-CSF variant of claim 1 which contains one oxygen atom at a methionine residue.

8. The oxidized GM-CSF variant of claim 1 which contains two oxygen atoms at methionine residues.

9. The oxidized GM-CSF variant of claim 1 which contains three oxygen atoms at methionine residues.

10. The oxidized GM-CSF variant of claim 1 which contains four oxygen atoms at methionine residues.

11. A method for making a biologically active oxidized GM-CSF variant having at least one oxidized methionine residue, comprising treating unoxidized GM-CSF with an oxidizing agent under conditions in which one or more methionine residues are oxidized.

12. The method of claim 11 in which the oxidizing agent is selected from the group consisting of $H_2O_2$, 2-(2-nitrophenylsulfenyl)-3-methyl-3-bromoindolenine, performic acid, sodium periodate and chloramine T.

13. A pharmaceutical composition comprising oxidized GM-CSF variant of claim 1 and a pharmaceutically acceptable carrier.

14. A method for treating an individual having a medical condition susceptible to treatment by GM-CSF comprising administering to such individual an effective amount of the oxidized GM-CSF variant of claim 1.

* * * * *